(12) United States Patent
Tickner et al.

(10) Patent No.: US 7,679,065 B2
(45) Date of Patent: Mar. 16, 2010

(54) DATA DISPLAY SYSTEM AND METHOD

(75) Inventors: James Richard Tickner, Meadows (AU); Yi Liu, Bexley (AU)

(73) Assignee: Commonwealth Scientific and Industrial Research Organisation, Act (AU)

( * ) Notice: Subject to any disclaimer, the term of this patent is extended or adjusted under 35 U.S.C. 154(b) by 115 days.

(21) Appl. No.: 11/659,364

(22) PCT Filed: Aug. 5, 2005

(86) PCT No.: PCT/AU2005/001174

§ 371 (c)(1),
(2), (4) Date: Aug. 24, 2007

(87) PCT Pub. No.: WO2006/012703

PCT Pub. Date: Feb. 9, 2006

(65) Prior Publication Data

US 2008/0135773 A1 Jun. 12, 2008

(30) Foreign Application Priority Data

Aug. 6, 2004 (AU) .............................. 2004904439

(51) Int. Cl.
*G01J 1/42* (2006.01)
(52) U.S. Cl. .................................................. 250/393
(58) Field of Classification Search ................ 250/393, 250/390.01–390.12; 378/53, 207
See application file for complete search history.

(56) References Cited

U.S. PATENT DOCUMENTS 6,740,887 B1 * 5/2004 Parvin et al. ................ 250/393

(Continued)

FOREIGN PATENT DOCUMENTS

AU    2003285991 B2    6/2004

(Continued)

OTHER PUBLICATIONS

Fink et al., "Evaluation of few-view reconstruction parameters for illicit substance detection using fast-neutron transmission spectroscopy," 1996, IEEE Transactions on nuclear science, vol. 43. No. 3. pp. 1352-1356.*

(Continued)

*Primary Examiner*—David P Porta
*Assistant Examiner*—Kiho Kim
(74) *Attorney, Agent, or Firm*—Sughrue Mion, PLLC

(57) ABSTRACT

Methods and systems are used to form an image of the contents of an object for display. A neutron mass attenuation matrix n and a gamma-ray mass attenuation matrix g are formed. A composition matrix and a density matrix are calculated whose respective elements $R_{ij}$ and $X_{ij}$ are each defined as a function of the elements $n_{ij}$ and the corresponding elements $g_{ij}$. $R_{ij}$ represents an average composition of material within the object between a source which generated the radiation and a point (i,j). $X_{ij}$ represents an approximate amount of material within the object between the radiation source and the point (i,j). A quality matrix is calculated whose elements $Q_{ij}$ are defined as a function of the elements $n_{ij}$ and the elements $g_{ij}$ and represents a measure of the reliability of the determination of the elements of $R_{ij}$. The image formed for display contains information from R, X, and Q.

49 Claims, 4 Drawing Sheets

U.S. PATENT DOCUMENTS

2002/0171042 A1* 11/2002 Chen et al. ............. 250/390.04

FOREIGN PATENT DOCUMENTS

WO      WO 90/16072 A1    12/1990
WO      WO 96/13839 A1    5/1996
WO      WO 2004/053472 A1    6/2004

OTHER PUBLICATIONS

Micklich et al., "Accelerator requirements for fast-neutron interrogation of luggage and cargo," 1995, IEEE Particle Accelerator Conference, vol. 1, pp. 110-112.*

Micklich et al., "Transport simulation and image reconstruction for fast-neutron detection of explosives and narcotics," 1995, Proceedings of SPIE, vol. 2511, pp. 33-44.*

Yule et al., "Fast neutron transmission spectroscopy for illicit substance detection," 1997, Proceedings of SPIE, vol. 2867, pp. 239-242.*

M. Elad, "On the Origin of the Bilateral Filter and Ways to Improve It", IEEE Transactions on Image Processing, vol. 11, No. 10, Oct. 2002.

C. Tomasi, et al., "Bilateral Filtering for Gray and Color Images", Proceedings of the 1998 IEEE International Conference on Computer Vision, Bombay, India.

* cited by examiner

DATA DISPLAY SYSTEM AND METHOD

TECHNICAL FIELD

The present invention concerns a method for processing transmission data from neutron and gamma-ray radiation to form an image, the neutron and gamma-ray radiation having traversed through an object and representing a measure of neutron attenuation and gamma-ray attenuation introduced by the object. The present invention further concerns a system for processing neutron and gamma-ray radiation data to form an image.

BACKGROUND ART

Conventional radiographic devices for security applications use X-ray or gamma-ray radiation to form images of scanned objects. If a single radiation energy is used, or a polychromatic source is used with a single detector system than cannot resolve the energy of the transmitted X-rays, only information about the density of the object is obtained. The image may be displayed using a gray-scale or a false-colour palette, but the choice of colour serves purely to enhance the visibility of subtle changes in density and does not convey information about object composition.

Dual-energy X-ray imaging systems are well know, employing either dual X-ray sources or dual X-ray detector systems that respond differently to different X-ray energies. By comparing the transmission of high and low energy X-rays, information about material composition can be inferred in addition to density. Images are typically presented using a fixed colour scale, with blues representing metals, greens mixed materials and browns organic substances. The main drawback of dual-energy X-ray systems is the limited penetration of lower energy X-rays, which limits their use to thinner and lighter objects such as packages and luggage.

Sowerby and Tickner [1] describe an imaging system using a combination of gamma-ray and fast neutron radiography to form density and composition images of thick objects such as air and sea cargos. They also describe a simple means of displaying images from this system, with composition mapped to colour hue and density mapped to colour brightness. However, this display system fails to make best use of the differences between the neutron and gamma-ray images to extract maximum information about the object being scanned. In particular, it does not handle the imaging of thick, highly attenuating cargo where one of either the neutron or gamma-ray radiation beams is totally blocked. Similarly, it fails to properly take into account the different noise levels on the neutron and gamma-ray images.

Noise removal from a given image is an important practical problem occurring in many applications, particularly in nuclear imaging processing.

Simple smoothing techniques of averaging pixels over their immediate neighbourhood is well known. However the main drawback of such a method is the loss of the image details by averaging. More recent methods for noise removal, such as bilateral filtering [2,3] which use a Bayesian approach as their theoretical foundation, have concentrated on preserving image detail whilst removing noise. It has been shown that the bilateral filter method is very effective in removing additive noise from images and it is simple to implement and does not require iteration.

DISCLOSURE OF INVENTION

In a first aspect, the invention is a method for processing transmission data from neutron and gamma-ray radiation to form an image, the neutron and gamma-ray radiation having traversed through an object and representing a measure of neutron attenuation and gamma-ray attenuation introduced by the object, the method comprising:

forming a neutron mass attenuation matrix from the measure of neutron attenuation;

forming a gamma-ray mass attenuation matrix from the measure of gamma-ray attenuation;

calculating a composition matrix R whose elements $R_{ij}$ are defined as a function of elements $n_{ij}$ from the neutron mass attenuation matrix and the corresponding elements $g_{ij}$ of the gamma-ray mass attenuation matrix, the composition matrix representing an average composition of material between a source which generated the radiation and a point (i,j);

calculating a density matrix X whose elements $X_{ij}$ are defined as a function of the elements $n_{ij}$ from the neutron mass attenuation matrix and the corresponding elements $g_{ij}$ from the gamma-ray mass attenuation matrix, the density matrix representing an approximate amount of material between the radiation source and the point (i,j);

calculating a quality matrix Q as a function of the elements $n_{ij}$ from the neutron mass attenuation matrix and the elements $g_{ij}$ of the gamma-ray mass attenuation matrix, the quality matrix representing a measure of the reliability of the elements of $R_{ij}$; and forming an image for display; wherein the image contains information from R, X and Q.

The elements of the neutron mass attenuation matrix may be calculated by taking the logarithm of the measured neutron attenuations. Similarly, the elements of the gamma-ray attenuation matrix may be calculated by taking the logarithm of the measured gamma-ray attenuations. An additional step of adding a small positive number to the measured attenuations before forming the logarithm may be used to ensure that the logarithm is always finite. The number may be an inherent machine accuracy parameter.

Forming the neutron mass attenuation matrix and the gamma-ray mass attenuation matrix may comprise a second step of truncating the elements of each of the neutron mass attenuation and gamma-ray mass attenuation matrices to a predetermined range.

Forming the neutron mass attenuation matrix and the gamma-ray mass attenuation matrix may further comprise a third step of scaling the elements of each of the neutron mass attenuation and gamma-ray mass attenuation matrices to a predetermined range, typically 0-1. The elements of the neutron mass attenuation matrix may be scaled according to a first scaling parameter and the elements of the gamma-ray mass attenuation matrix may be scaled according to a second scaling parameter. The first and second scaling parameters may not be equal. It may be advantageous to set the first scaling parameter lower than the second scaling parameter if the measure of neutron attenuation is found to contain significant statistical noise.

Forming the neutron mass attenuation matrix and the gamma-ray mass attenuation matrix may further comprise a fourth step of applying a spatial filter for smoothing to the elements of each of the neutron mass attenuation and gamma-ray mass attenuation matrices. This step may comprise the step of calculating the difference between neighbouring elements and applying the filter if the difference is less than a predetermined value. An advantage of such a step is that edge preservation may be enhanced.

Forming the neutron mass attenuation matrix and the gamma-ray mass attenuation matrix may further comprise a fifth step of scaling the elements of each of the neutron mass attenuation and gamma-ray mass attenuation matrices to a predetermined range. This step may be necessary if, in the third step, the first and second scaling parameters are not equal. The predetermined range may be the same as that in the third step.

In one example, calculating the composition matrix R may comprise forming a new matrix g' by the step of adding a constant value to each of the elements of the gamma-ray attenuation matrix g to ensure that each of the elements is non zero. The constant value may be an inherent machine parameter. The composition matrix R may then be calculated as an element-by-element ratio of the neutron mass attenuation matrix to the new matrix g'.

In a second example, calculating the composition matrix R may comprise the initial step of calculating the sum of each element from the neutron mass attenuation matrix with the corresponding element from gamma-ray mass attenuation matrix and then calculating a ratio of the elements from the neutron mass attenuation matrix to this sum of elements. When calculating the sum of each element from each matrix a data parameter may be added to ensure that the sum of any pair of elements is non zero.

In either example, calculating R may further comprise the step of truncating each of the elements of R to a predetermined range.

In a preferred embodiment, the step of calculating R may further comprise the step of applying a spatial filter for smoothing to the composition matrix R to reduce statistical noise, whilst preserving edges which convey important information about objects being imaged. Accordingly, each element of R may be replaced by a normalised, weighted sum of the elements in its immediate vicinity. Each weight may be calculated as a product of two functions, one a function of the geometric distance between the element being replaced and its neighbourhood elements, which ensures that close-by elements influence the final weight more than distant elements and the other a function of the radiometric distance between the element being replaced and the neighbouring elements, which ensures that the elements with similar attenuation values influence the final result more than elements with distant values. The geometric distance between the centre element and its neighbouring elements may be calculated using a Euclidean metric and non-square neighbourhood may be allowed in case the vertical resolution of R is different from the horizontal resolution. The radiometric distance between the centre element and its neighbouring elements may be calculated using a Euclidean metric based on the absolute or fractional differences in attenuation values between the centre element and its neighbouring elements. Such a filter has the advantage of reducing statistical noise in flat image regions whilst simultaneously preserving edges of objects being imaged.

In the calculation of the density matrix X it is desirable to weight each element of the neutron and gamma-ray mass attenuation matrices such that the measure of gamma-ray attenuation dominates the measure of neutron attenuation for the majority of pixels. Only where the gamma-ray attenuation is significantly greater than the neutron attenuation, such that the precision of the neutron attenuation measurement exceeds that of the gamma-ray measurement, should the neutron attenuation information contribute significantly to the determination of X. The calculation of each element $X_{ij}$ may comprise forming a weighted sum of the gamma-ray ($g_{ij}$) and neutron ($n_{ij}$) attenuations, with the weights chosen to favour the gamma-ray attenuation measurement except for those elements where $n_{ij}$ is substantially better determined than $g_{ij}$. Advantageously, this method allows imaging through thick metal objects where gamma-rays are strongly attenuated.

In a preferred embodiment, the method may further comprise applying a spatial filter for sharpening to the density matrix X to increase the definition and sharpness of object edges without increasing statistical noise in flat regions of the image. Preferably this filter for sharpening is complementary to the smoothing filter described previously. Accordingly, each element of X may be replaced by a normalised weighted sum of the elements in its immediate vicinity. Each weight is calculated as a product of two functions, one of geometric distance and one of radiometric distance, where the calculation and the application of the geometric distance function is the same as described before. The calculation of the radiometric distance function may comprise the step of calculating the absolute or fractional attenuation differences between the centre element and its neighbouring elements and applying the sharpening function such that elements with similar attenuation values influence the final sharpening result less than elements with significantly different values. An advantage of such a step is that noise in flat regions of the image is not increased while the details in the image are enhanced.

Calculating the quality matrix Q may involve calculating a function whose value is close to 1 except when either $n_{ij}$ or $g_{ij}$ is close to either 1 or 0. Advantageously, when any element $n_{ij}$ or $g_{ij}$ is close to 1 (indicating large attenuation) or close to 0 (minimal attenuation), with potentially large errors, $Q_{ij}$ tends to 0. Consequently, the quality matrix element $Q_{ij}$ is close to unity when the corresponding element $R_{ij}$ is well determined and is close to zero when the corresponding element $R_{ij}$ is poorly determined.

The method may include a preliminary step of correcting the measure of neutron and gamma-ray attenuation to minimize geometric distortion arising from the configuration of the radiation sources.

This step of applying a geometric correction to the measure of neutron or gamma-ray attenuation may comprise:

recording the measure of neutron or gamma-ray transmission, the measure comprising a plurality of count rates each which correspond to data obtained from a single detector pixel;

calibrating the recorded measure of neutron or gamma-ray transmission by dividing each count rate by count rates observed when no materials lies between the source and detector pixels;

applying a first correction factor to the calibrated measure of neutron or gamma-ray attenuation to correct for data which corresponds to an inoperative pixel;

applying a second correction factor to the calibrated measure of neutron or gamma-ray attenuation to correct for data which is indicative of neutron or gamma-ray scattering;

if the detector arrays comprise multiple columns of pixels, interpolating the attenuations measured using these multiple vertical columns to a position corresponding to the geometric centre of the columns and combining these attenuations to calculate a single average attenuation at a position in the object corresponding to the geometric centre of the columns; and projecting and interpolating the corrected measure of neutron or gamma-ray attenuation onto a uniformly spaced grid on a cylindrical surface, whose axis passes through the source and is normal to the plane containing both the source and a line parallel to the neutron detector columns, passing through the geometric centre of the columns, whilst allowing for non-uniform pixel separation.

Forming an image for display may comprise a first step of converting the composition matrix R, the quality matrix Q and the density matrix X to an HSL (Hue, Saturation, Luminosity) colour space and a second step of converting the HSL colour space to an RGB colour space for display. The image may be displayed on a monitor such as a computer monitor or other like monitor, or may be output to a printer device. Of course different colour spaces other than the RGB colour space may be used.

Converting the composition matrix R, the saturation matrix S and the density matrix X to the HSL colour space may involve mapping each of the elements of R to H, Q to S and X to L. The hue of a pixel in the final image then corresponds to the composition of material for that pixel. The pixel brightness corresponds to the mass of material for that pixel. Pixels with little or no material appear white; pixels with large amounts of material appear black; intermediate pixels are coloured according to the value of R. Advantageously, the colouration of pixels where R is poorly determined due to too little or too much material being present in the radiation beams are largely unaffected by the value of R. The colouring of pixels with poorly determined R values is further suppressed, as such pixels will have small saturation (S) values, causing them to be displayed as a shade of grey. Advantageously, the value of S can be set to zero for every pixel, producing a grey scale image, which emphasises structural information at the cost of suppressing composition information. Further, S values for pixels having low/high R values can be set to zero, emphasising regions of the image comprising primarily inorganic (low R) or organic (high R) materials.

In a second aspect, the invention is a system for processing neutron and gamma-ray transmission data to form an image, the system comprising:

a data input means to receive neutron and gamma-ray radiation having traversed through an object and representing a measure of neutron attenuation and gamma-ray attenuation introduced by the object; and a processor to:

form a neutron mass attenuation matrix from the measure of neutron attenuation;

form a gamma-ray mass attenuation matrix from the measure of gamma-ray attenuation;

calculate a composition matrix R whose elements $R_{ij}$ are defined as a function of elements $n_{ij}$ from the neutron mass attenuation matrix and the corresponding elements $g_{ij}$ of the gamma-ray mass attenuation matrix, the composition matrix representing an average composition of material between a source which generated the radiation and a point (i,j);

calculate a density matrix X whose elements $X_{ij}$ are defined as a function of the elements $n_{ij}$ from the neutron mass attenuation matrix and the corresponding elements $g_{ij}$ from the gamma-ray mass attenuation matrix, the density matrix representing an approximate amount of material between the radiation source and the point (i,j);

calculate a quality matrix Q as a function of the elements from the neutron mass attenuation matrix and the elements of the gamma-ray mass attenuation matrix, the quality matrix representing a measure of the reliability of the elements of $R_{ij}$;

form an image for display; wherein the image contains information from R, X and Q.

The system may further comprise a display means for displaying the image.

The display means may be a monitor such as a computer monitor or other like monitor. Optionally the display means may be a printer device.

The processor may form an image for display by converting the composition matrix R, the quality matrix Q and the density matrix X to an HSL (Hue, Saturation, Luminosity) colour space and converting the HSL colour space to an RGB colour space.

The processor may be operable to convert the composition matrix R, the saturation matrix S and the density matrix X to the HSL colour space by mapping each of the elements of R to H, Q to S and X to L.

The processor may be operable to correct the measure of neutron and gamma-ray attenuation so as to minimize geometric distortion arising from the configuration of the radiation sources and detectors.

The processor may be operable to calculate the elements $n_{ij}$ of the neutron mass attenuation matrix and the elements $g_{ij}$ of the gamma-ray attenuation matrix by taking the logarithm of the measured neutron attenuations and the logarithm of the measured gamma-ray attenuations respectively. The processor may be further operable to add a positive number to the measured attenuations prior to forming the logarithm to ensure that the logarithm is finite.

The processor may be operable to truncate the elements of each of the neutron mass attenuation and gamma-ray mass attenuation matrices to a predetermined range to remove elements having negative values. The processor may be further operable to scale the neutron and gamma-ray mass attenuation matrices to a range 0 to 1. The processor may be operable to calculate two copies of both the neutron and gamma-ray mass attenuation matrices, one having a spatial resolution substantially equal to that of the neutron image and one with a spatial resolution substantially equal to that of the gamma-ray image, where these two resolutions are different.

The processor may be operable to calculate the elements of the composition matrix R according to the formula $R_{ij} = (a_1 n_{ij} + a_2 g_{ij})/(a_3 n_{ij} + a_4 g_{ij} + e)$ where $a_1$, $a_2$, $a_3$, $a_4$ are weighting parameters and e is a small positive number chosen to prevent the denominator tending to zero. In an embodiment, $a_1 = a_3 = a_4 = 1$ and $a_2 = 0$. In a further embodiment $a_1 = a_4 = 1$ and $a_2 = a_3 = 0$. The elements of the composition matrix R may be calculated from the neutron and gamma-ray mass attenuation matrices with the lowest spatial resolution.

The processor may be further operable to apply a spatial filter for smoothing to the neutron and gamma-ray mass attenuation matrices before calculating the composition matrix R.

The processor may be further operable to apply a spatial filter for smoothing to the calculated composition matrix R.

The spatial filters for smoothing may replace each element with a normalised, weighted average of neighbouring elements, where the weights are computed as a product of a geometric distance function and a radiometric distance function such that an element with closer geometric and radiometric distances from a central element has a stronger influence on the smoothing result, where geometric distances are calculated using true distances between the central element and its neighbouring elements which are independent of image resolutions and the radiometric distances are calculated by absolute or fractional differences of the attenuations values between the central element and its neighbouring elements.

The processor may be further operable to calculate the elements of the density matrix X according to the formula $X_{ij} = g_{ij} * f(g_{ij}) + b * n_{ij} * (1 - f(g_{ij}))$, where f(.) is a function which is substantially equal to unity over most of its range but tends to zero as its argument tends to 1 and b is a weighting parameter that accounts for the different attenuations of gamma-rays and neutrons. b may be a fixed parameter. Alternatively b may be calculated as a function of the matrix element $R_{ij}$.

The function f(x) preferably has the form $(1-x)^p$ where the exponent p lies in the range 0-11.

Elements of the density matrix X may be calculated from the neutron and gamma-ray mass attenuation matrices with the highest spatial resolution.

The processor may be further operable to apply a spatial filter for smoothing to the neutron and gamma-ray mass attenuation matrices before calculating the density matrix X.

The processor may be further operable to apply a spatial filter for sharpening to the calculated density matrix X. The filter for sharpening may replace each element with a normalised weighted average of neighbouring elements, where the weights are computed as a product of a geometric distance function and a radiometric distance function such that an element with a closer geometric distance and a greater radiometric distance from a central element has stronger influence on sharpening result, where the geometric distances are calculated using the true distances between the central element and its neighbouring elements which are independent of image resolutions and the radiometric distances are calculated by absolute or fractional differences of the attenuation values between the central element and its neighbouring elements.

The processor may be further operable to calculate the elements of the quality matrix Q according to the formula $Q_{ij}=q(n_{ij},g_{ij})$, where the function q(.) is substantially equal to unity except for where either of its arguments tends to either 0 or 1, in which case the value of q(.) tends to zero. In at least one embodiment, q(.) has the function form $Q_{ij}=[(n_{ij}/2+g_{ij})*(1-n_{ij})/2+(1-g_{ij})]^\alpha$, or $Q_{ij}=(n_{ij}*g_{ij})^\alpha*[\max(1-n_{ij},\ 1-g_{ij})]^\beta$, where $\alpha$ and $\beta$ are small positive real numbers.

The processor may be further operable to calculate the elements of the quality matrix Q from the neutron and gamma-ray mass attenuation matrices with the lowest spatial resolution.

The processor may be further operable to interpolate the composition matrix R and quality matrix Q to increase the resolution so as to match the resolution of the density matrix X.

In a third aspect, the invention is a computer program comprising computer program code adapted to perform the method of any of the embodiments above, when the program is run on a computer. The computer program may be embodied on a computer readable medium.

The processor may be operable to correct the measure of neutron and gamma-ray mass attenuation to minimize geometric distortion arising from the configuration of the radiation sources and detectors.

An advantage of at least one embodiment of the invention is that it is able to handle multiplicative noise removal of transmission data from neutron and gamma-ray radiation. A further advantage of at least one embodiment of the invention utilising the sharpening filter is such that details of the image are enhanced without substantially increasing the statistical noise in the flat region of the image.

BRIEF DESCRIPTION OF DRAWINGS

An example of the invention will now be described with reference to the accompanying drawings.

BEST MODE FOR CARRYING OUT THE INVENTION

Figure 1:
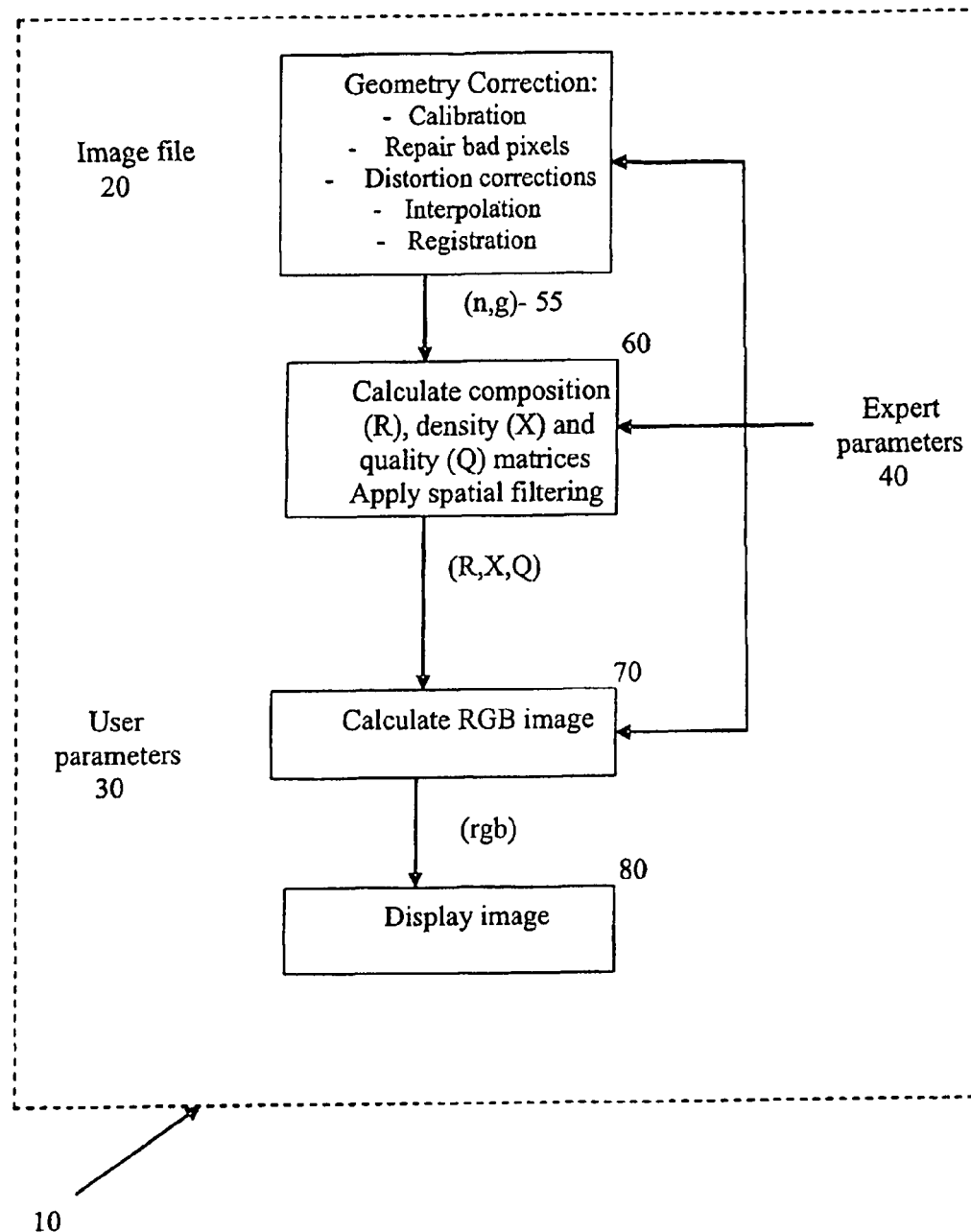
FIG. 1 illustrates a schematic outline of a method 10 for processing image data from neutron and gamma-ray radiation having traversed through an object such as a unit load device ULD.

FIG. 1 illustrates a schematic outline of a method 10 for processing image data from neutron and gamma-ray radiation having traversed through an object such as a unit load device ULD. The image data represents a measure of neutron attenuation and gamma-ray attenuation introduced by the ULD.

To obtain the image data, the ULD is scanned through radiographic equipment. The equipment includes two separate generators of radiation. The first is a sealed tube neutron generator having a D-T neutron emitting module to produce a neutron energy source having an energy of substantially 14 MeV. The second generator of radiation is a $^{60}$Co source to produce a source of gamma-rays having an energy of substantially 1 MeV. Both sources are situated within a shield housing which has a collimating slit cut into the shield to generate fan shaped radiation. A detector array is situated opposite the radiation sources and is housed in a detector shield which also has cut into it a collimating slit. The detector array comprises columns of scintillator pixels.

Between the sources and detector is a tunnel. The ULD to be imaged is mounted on a platform that has runners that engage a pair of tracks. The platform is driven through the tunnel and a scintillation spectrum is collected for each element of the pixel array. Alternatively, the ULD may be positioned on a conveyor belt or rollers and driven through the tunnel, with scintillation spectra similarly collected. The spectra are read out and reset every time the platform traverses a predetermined distance and the spectra are used to deduce neutron and gamma-ray count rates for each pixel. The count rates in each vertical strip are then assembled to form complete 2D images of neutron and gamma-ray count rates.

In order to process the 2D images of neutron and gamma-ray count rates, three inputs are read into a processor. The first input, an image file 20, contains the images of the neutron and gamma-ray count rates, calibration information, geometry information for the detector array, a bad-pixel list and ancillary non-image information. The calibration information includes information as to the neutron intensity and gamma-ray intensities detected in a pixel without the ULD present. The geometry information includes information relating to at least the number of columns in the image file, the distance between the columns, the x co-ordinate positions of the pixels, and the y co-ordinate positions of the pixels.

The ancillary non-image information includes an identifier for the ULD, a flight number identifier on which the ULD was transported, a scanner operator identifier, a date stamp and a time stamp for when the ULD scan was completed, a date stamp and a time stamp for when the ULD file was first viewed and an identifier of the operator who first viewed the file.

The second input comprises a list of user adjustable parameters 30 which include an image brightness control, a contrast control and a colouration control. The third input comprises a list of expert parameters 40 controlling the formation and scaling of the neutron and gamma-ray mass attenuation matrices, neutron and gamma-ray scattering corrections, spatial filters for sharpening and smoothing and colour mapping.

Figure 2:
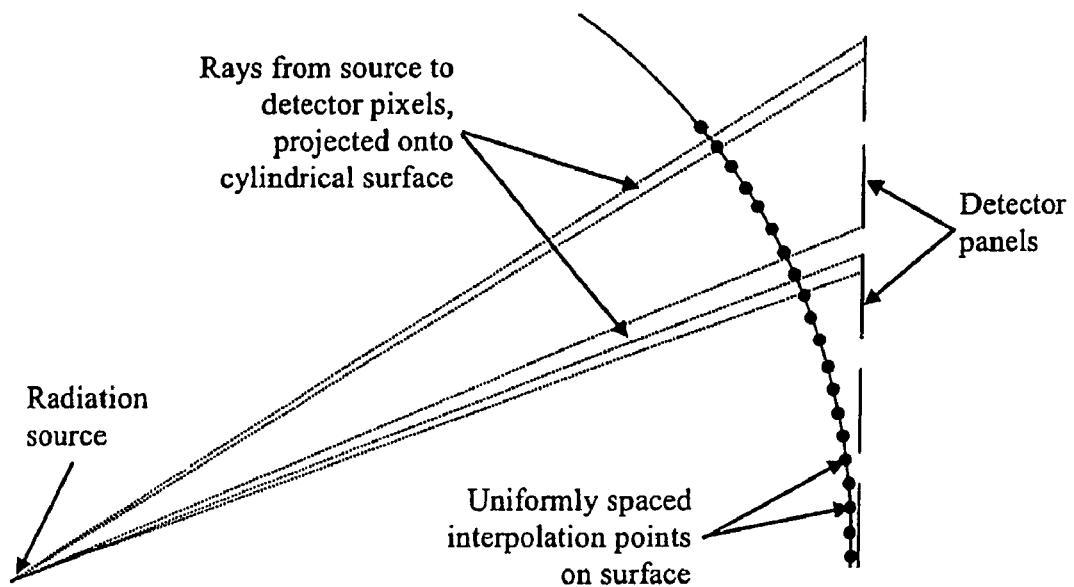
FIG. 2 illustrates a means for correcting for geometric distortion introduced by non-uniform separation between detector pixels.
Figure 3:
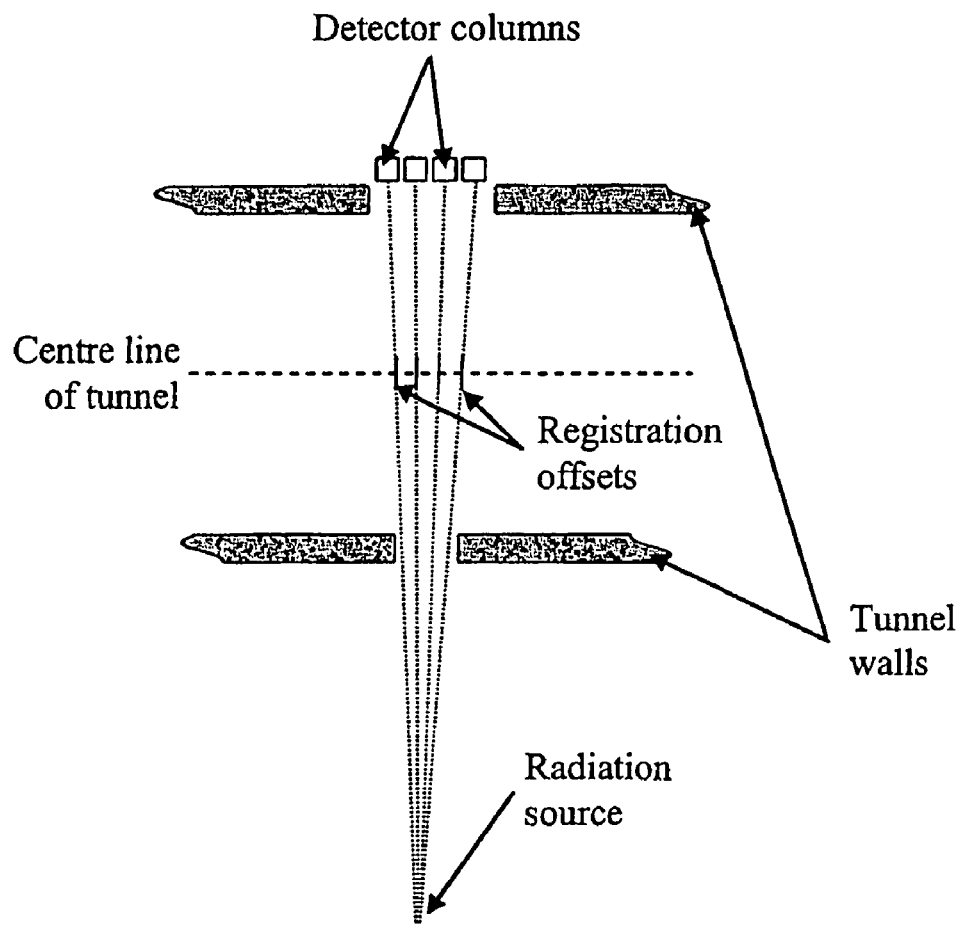
FIG. 3 illustrates a means for combining the output of multiple columns of detector pixels.

Processing the neutron and gamma-ray count rates includes a first step 50, (illustrated in FIGS. 2 and 3) of geometric correction and summation to produce output matrices n and g 55, a second step 60 which takes the output from the first step and infers the matrices R, X and Q where R is a measure of the composition of contents of the ULD, X is a measure of the density of the ULD and Q is a quality parameter to provide an indication of the reliability of R, a third step 70 of calculating an RGB image from R, X and Q and a fourth step 80 of displaying the RGB image on a monitor.

To perform the first step of geometric correction 50, the calibration information is applied to the neutron and gamma-ray count rates. A correction factor is applied to the calibrated measures of neutron and gamma-ray count rates to correct for data which corresponds to any bad or missing pixels. A further correction factor is then applied to correct for data which is indicative of neutron scattering and gamma-ray scattering respectively. The corrected measures of neutron and gamma-ray count rates form a neutron attenuation matrix n and a gamma-ray attenuation matrix g which are then interpolated onto a uniformly spaced grid whilst allowing for any non-uniform pixel separation.

Two copies of both the neutron and gamma-ray attenuation matrices n and g are calculated, one with resolution substantially equal to the resolution of the gamma-ray image and one with resolution substantially equal to the lower resolution of the neutron image.

The second step 60, infers the matrices R, X and S. The neutron attenuation matrix n, gamma-ray attenuation matrix g and expert parameters are inputs into the processor.

Formation of R

The calculation of the R matrix proceeds using the lower resolution copies of the n and g matrices. A small machine number is added to each of the elements of the neutron attenuation matrix n and gamma-ray attenuation matrix g. New matrices N and G are formed by taking the logarithms of each element of the respective matrices. In the event that any element of n or g is zero the small machine number will ensure that the logarithm of that value does not tend to infinity. Both matrices N and G are then clamped within a reasonable range to ensure that the final image does not contain non-negative elements.

N and G are then scaled to [0,1] and a spatial filter for smoothing is applied. The filter for smoothing acts to preserve the edges whilst reducing noise in flat regions of the image. The filter replaces each element with a weighted average of its neighbouring elements, with the weights calculated as the product of two functions. The first is a function of the geometric distance between the weighted element and the element to be replaced; the second is a function of the radiometric distance. Advantageously, this filter reduces noise whilst preserving object details such as edges.

The elements of the matrix N are then scaled back to their original scale to form matrix nn and the elements of the matrix G are then scaled back to their original scale to form matrix gg. The parameter R is then calculated as a ratio of the elements from the neutron mass attenuation matrix nn to a denominator. To form the denominator, the elements of nn are summed with the corresponding element of gg together with a small machine number. Thereafter, the elements of R are clamped to within a reasonable range to ensure that subsequent calculations do not render absurd figures and a spatial filter for smoothing as described above is then applied.

The final step is to interpolate R matrix to match the spatial resolution of the gamma-ray image.

Formation of X

The calculation of the X matrix proceeds using the higher resolution copies of the n and g matrices. A small machine number is added to each of the elements of the neutron attenuation matrix n and gamma-ray attenuation matrix g. New matrices N and G are formed by taking the logarithms of each element of the respective matrices. In the event that any element of n or g is zero the small machine number will ensure that the logarithm of that value does not tend to infinity. Both matrices N and G are then clamped within a reasonable range to ensure that the final image does not contain non-negative elements.

N and G are then scaled to [0,1] and a spatial filter for smoothing is applied. The smoothing filter acts to preserve the edges whilst reducing noise in flat regions of the image. The smoothing filter replaces each element with a weighted average of its neighbouring elements, with the weights calculated as the product of two functions. The first is a function of the geometric distance between the weighted element and the element to be replaced; the second is a function of the radiometric distance. Advantageously, this filter reduces noise whilst preserving object details such as edges. The elements of the density matrix X are then calculated according to the formula $X_{ij}=G_{ij}*f(g_{ij})+b*N_{ij}*(1-f(g_{ij}))$ where $f(x)$ is a function of form $(1-x)^p$, where p is typically a small number between (0.05 and 0.1) and b is a weighting parameter that accounts for the different attenuations of gamma-rays and neutrons.

A spatial filter for sharpening is then applied. The filter acts to increase image definition without increasing noise. The filter replaces each element with a weighted average of its neighbouring elements, with the weights calculated as the product of two functions. The first is a function of the geometric distance between the weighted element and the element to be replaced; the second is a function of the radiometric distance.

Formation of Q

The elements of the quality matrix Q are calculated from the smoothed, scaled matrices N and G calculated previously for the determination of the density matrix X. Elements of Q are calculated according to formula $Q_{ij}=\{(N_{ij}/2+G_{ij})*[(1-N_{ij})/2+(1-G_{ij})]\}^\alpha$, where $\alpha$ is small positive real number (between 0.05 and 0.1).

Advantageously, when both elements of n and g are close to 0 or 1, Q tends to 0 and the quality of that particular element of R cannot be guaranteed.

The third step 70, infers the quantities R, G and B. R, X, Q, user parameters 30 and expert parameters 40 are inputs into the processor. R, X, and Q are mapped to colour space HSL. The HSL colour space is then mapped to RGB. The resultant image is then displayed.

The first 50 and second 60 steps are performed once for each image at the time that the image is accessed. Steps three 70 and four 80 are performed whenever the user controls are adjusted by an operator.

Figure 4:
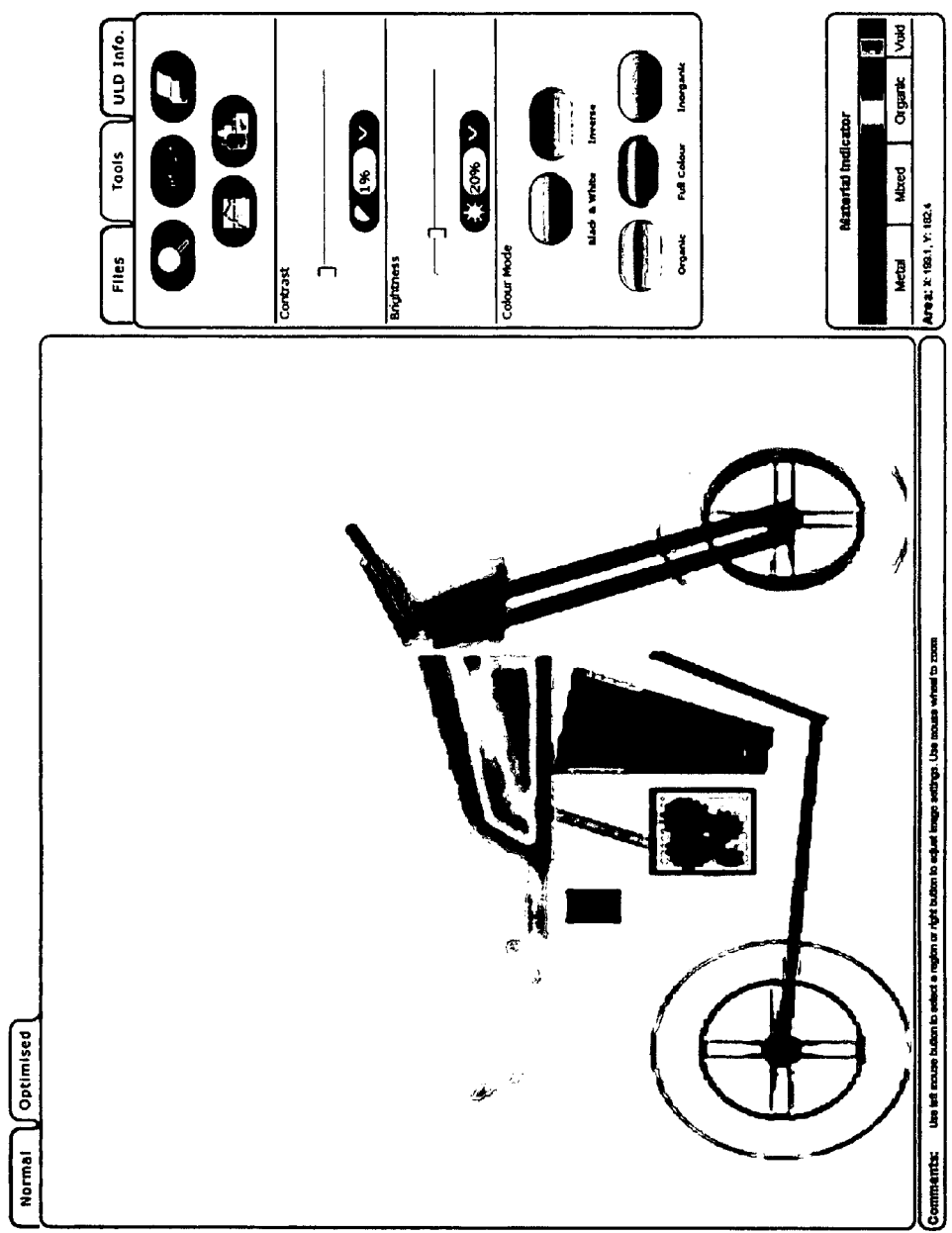
FIG. 4 is a schematic illustration of a user operated graphical display.

FIG. 4 schematically illustrates a graphical display 100 operable by an operator and displaying a single image of the interior contents of a ULD, which in this case contains a simulated image of a motorcycle 102. A screen menu 104 on the right hand side of the display 100 enables the operator to selectively access submenus: 'Files' 106, 'Tools' 108, and 'ULD information' 110. This particular display illustrates the 'Tools' 108 submenu. Slider scales are provided to enable the operator to modify the contrast 112 and brightness 114 of the ULD under consideration. This information is also provided to the operator in the form of percentages 116. The operator is provided with a colour mode option enabling the selection of the image in 'black and white' 118, 'full colour' 122, 'inorganic' 124 and an 'inverse' 126 perspective. An enhanced 'organic' 120 image is also presented. Selection of this feature emphasises organic regions of the image, which are coloured yellow, orange and red.

Colour images in particular distinguish a wide variety of inorganic and organic materials. The density of colour shows the material density with white corresponding to no intervening material and denser regions having a saturated colour.

At the bottom of the screen is a 'material indicator bar' 128 to enable the operator to quickly determine the composition of the object(s) within the ULD by association by colour. For example, the frame 130 and spokes 132 of the motorcycle 102 are indicated to be of a metallic composition 133 whereas the seat 134 and fuel tank 136 are shown to be of an organic composition 138. Materials of mixed composition 140 may also be identified. Of course this illustration is merely illustrative and the 'material indicator bar' 128 may identify a range of colours and or tones to differentiate materials.

A control to vary the magnification 138 is provider as is a control to enable a screen dump 140, a control to display a graphical analysis 142 and a default setting 144 to enable the operator to program specified settings. In addition the operator can view the image under normal 146 or optimised 148 conditions. Of course this illustration is merely illustrative and the graphical display could embody many different forms to enhance operator usability.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

[1] B. Sowerby and J. Tickner, "Radiographic equipment", Australian Standard Patent Application 2003285991.
[2] C. Tomasi and R. Manduchi, "Bilateral filtering for gray and color images," in *Proc. 6$^{th}$Int. Conf. Computer Vision*, New Delhi, India, 1998, pp. 839-846.
[3] M. Elad, "On the origin of the bilateral filter and ways to improve it", *IEEE Trans. Image Processing*, vol. 11, no. 10, October, 2002.

The invention claimed is:

1. A method for processing transmission data from neutron and gamma-ray radiation to form an image of an object's contents, the neutron and gamma-ray radiation having traversed through the object and representing a measure of neutron attenuation and gamma-ray attenuation introduced by the object, the method comprising:
   forming a neutron mass attenuation matrix n from the measure of neutron attenuation;
   forming a gamma-ray mass attenuation matrix g from the measure of gamma-ray attenuation;
   calculating a composition matrix R whose elements $R_{ij}$ are defined as a function of the elements $n_{ij}$ from the neutron mass attenuation matrix and the corresponding elements $g_{ij}$ from the gamma-ray mass attenuation matrix, the composition matrix representing an average composition of material within the object between a source which generated the radiation and a point (i,j);
   calculating a density matrix X whose elements $X_{ij}$ are defined as a function of the elements $n_{ij}$ from the neutron mass attenuation matrix and the corresponding elements $g_{ij}$ from the gamma-ray mass attenuation matrix, the density matrix representing an approximate amount of material within the object between the radiation source and the point (i,j);
   calculating a quality matrix Q whose elements $Q_{ij}$ are defined as a function of the elements $n_{ij}$ from the neutron mass attenuation matrix and the elements $g_{ij}$ of the gamma-ray mass attenuation matrix, the quality matrix representing a measure of the reliability of the determination of the elements of $R_{ij}$; and
   forming an image of the contents of the object for display; wherein the image contains information from R, X, and Q.

2. A method according to claim 1, further comprising a preliminary step of correcting the measure of neutron and gamma-ray attenuation so as to minimize geometric distortion arising from the configuration of the radiation sources and detectors.

3. A method according to claim 2, where the step of correcting the measure of neutron or gamma-ray attenuation comprises:
   recording the measure of neutron or gamma-ray transmission, the measure comprising a plurality of count rates each which correspond to data obtained from a single detector pixel;
   calibrating the recorded measure of neutron or gamma-ray attenuation by dividing each measured count-rate by count-rates previously measured in the absence of intervening material;
   applying a first correction factor to the calibrated measure of neutron or gamma-ray attenuation to correct for data which corresponds to an inoperative pixel;
   applying a second correction factor to the calibrated measure of neutron or gamma-ray attenuation to correct for data which is indicative of neutron or gamma-ray scattering;
   if the transmission data is collected from detector arrays which comprise multiple columns of pixels, interpolating the attenuations measured using these multiple columns to a position corresponding to the geometric centre of the columns and combining these attenuations to calculate a single average attenuation at a position in the object corresponding to the geometric centre of the columns; and
   projecting and interpolating the corrected measure of neutron or gamma-ray attenuation onto a uniformly spaced grid on a cylindrical surface, whose axis passes through the source and is normal to the plane containing both the source and a line parallel to the neutron detector columns, passing through the geometric centre of the columns, whilst allowing for non-uniform pixel separation.

4. A method according to any one of the preceding claims, where the elements $n_{ij}$ of the neutron mass attenuation matrix and the elements $g_{ij}$ of the gamma-ray attenuation matrix are calculated by taking the logarithm of the measured neutron attenuations and the logarithm of the measured gamma-ray attenuations respectively.

5. A method according to claim 4, further comprising adding a positive number to the measured attenuations prior to forming the logarithm to ensure that the logarithm is finite.

6. A method according to claim 1, where forming the neutron mass attenuation matrix n and the gamma-ray mass attenuation matrix g comprises truncating the elements of each of the neutron mass attenuation and gamma-ray mass attenuation matrices to a predetermined range to remove elements having negative values.

7. A method according to claim 6, further comprising scaling the neutron and gamma-ray mass attenuation matrices to the range 0-1.

8. A method according to claim 7, where two copies of both the neutron and gamma-ray mass attenuation matrices are calculated, one with a spatial resolution substantially equal to that of the neutron image and the other with a spatial resolution substantially equal to that of the gamma-ray image, where these two resolutions are different.

9. A method according to claim 8, further comprising calculating the elements of the composition matrix R according to the formula $R_{ij}=(a_1 n_{ij}+a_2 g_{ij})/(a_3 n_{ij}+a_4 g_{ij}+e)$, where $a_1$, $a_2$, $a_3$, $a_4$ are weighting parameters and e is a positive number chosen to prevent the denominator tending to zero.

10. A method according to claim 9, further comprising calculating the elements of the composition matrix R from the neutron and gamma-ray mass attenuation matrices with the lowest spatial resolution.

11. A method according to claim 10, further comprising applying a spatial filter for smoothing to the calculated composition matrix R.

12. A method according to claim 11, where the filter for smoothing replaces each element with a normalised, weighted average of neighbouring elements, where the weights are computed as a product of a geometric distance function and a radiometric distance function such that an element with closer geometric and radiometric distances from a central element has a stronger influence on the smoothing result, where geometric distances are calculated using true distances between the central element and its neighbouring elements which are independent of image resolutions and the radiometric distances are calculated by absolute or fractional differences of the attenuation values between the central element and its neighbouring elements.

13. A method according to claim 9, further comprising applying a spatial filter for smoothing to the neutron and gamma-ray mass attenuation matrices before calculating the composition matrix R.

14. A method according to claim 1, further comprising calculating the elements of the density matrix X according to the formula $X_{ij}=g_{ij}*f(g_{ij})+b*n_{ij}*(1-f(g_{ij}))$, where $f(g_{ij})$ is a function which is substantially equal to unity over most of its range but tends to zero as its argument tends to 1 and b is a weighting parameter that accounts for the different attenuations of gamma-rays and neutrons.

15. A method according to claim 14 where b is a fixed parameter.

16. A method according to claim 15 where the function $g(g_{ij})$ has the form $(1-x)^p$ where the exponent p lies in the range 0-1.

17. A method according to claim 16, further comprising calculating the elements of the density matrix X from the neutron and gamma-ray mass attenuation matrices with the highest spatial resolution.

18. A method according to claim 14, further comprising applying a spatial filter for smoothing to the neutron and gamma-ray mass attenuation matrices before calculating the density matrix X.

19. A method according to claim 18, further comprising applying a spatial filter for sharpening to the calculated density matrix X.

20. A method according to claim 19 where the spatial filter for sharpening replaces each element with a normalised weighted average of neighbouring elements, where the weights are computed as a product of a geometric distance function and a radiometric distance function such that an element with a closer geometric distance and a greater radiometric distance from a central element has stronger influence on sharpening result, where the geometric distances are calculated using the true distances between the central element and its neighbouring elements which are independent of image resolutions and the radiometric distances are calculated by absolute or fractional differences of the attenuation values between the central element and its neighbouring elements.

21. A method according to claim 1, further comprising calculating the elements of the quality matrix Q according to the formula $Q_{ij}=q(n_{ij},g_{ij})$, where the function $q(n_{ij},g_{ij})$ is substantially equal to unity except for where either of its arguments tends to either 0 or 1, in which case the value of $g(n_{ij},g_{ij})$ tends to zero.

22. A method according to claim 21 where $q(n_{ij},g_{ij})$ has the function form $Q_{ij}=[n_{ij}/2+g_{ij})*(1-n_{ij})/2+(1-g_{ij})]^\alpha$, or $Q_{ij}=(n_{ij}*g_{ij})^\alpha *[\max(1-n_{ij}, 1-g_{ij})]^\beta$, where $\alpha$ and $\beta$ are positive real numbers.

23. A method according to claim 22, further comprising calculating the elements of the quality matrix Q from the neutron and gamma-ray mass attenuation matrices with the lowest spatial resolution.

24. A method according to claim 1, further comprising interpolating the composition matrix R and quality matrix Q to increase the resolution of these matrices so as to substantially match the resolution of the density matrix X.

25. A computer program comprising computer program code adapted to perform the method of claim 1 when the program is run on a computer.

26. A computer program as claimed in claim 25 embodied on a computer readable medium.

27. A system for processing neutron and gamma-ray transmission data to form an image, the system comprising:
 a data input device to receive neutron and gamma-ray radiation having traversed through an object and representing a measure of neutron attenuation and gamma-ray attenuation introduced by the object;
 a processor to:
  form a neutron mass attenuation matrix from the measure of neutron attenuation;
  form a gamma-ray mass attenuation matrix from the measure of gamma-ray attenuation;
  calculate a composition matrix R whose elements $R_{ij}$ are defined as a function of elements $n_{ij}$ from the neutron mass attenuation matrix and the corresponding elements $g_{ij}$ of the gamma-ray mass attenuation matrix, the composition matrix representing an average composition of material between a source which generated the radiation and a point (i,j);
  calculate a density matrix X whose elements $X_{ij}$ are defined as a function of the elements $n_{ij}$ from the neutron mass attenuation matrix and the corresponding elements $g_{ij}$ from the gamma-ray mass attenuation matrix, the density matrix representing an approximate amount of material between the radiation source and the point (i,j);
  calculate a quality matrix Q as a function of the elements from the neutron mass attenuation matrix and the elements of the gamma-ray mass attenuation matrix, the quality matrix representing a measure of the reliability of the elements of $R_{ij}$;
  form an image for display; wherein the image contains information from R, X, and Q.

28. A system according to claim 27, wherein the processor is further operable to correct the measure of neutron and gamma-ray attenuation so as to minimize geometric distortion arising from the configuration of the radiation sources and detectors.

29. A system according to claim 28 where the processor is further operable to calculate the elements $n_{ij}$ of the neutron mass attenuation matrix and the elements $g_{ij}$ of the gamma-ray attenuation matrix by taking the logarithm of the measured neutron attenuations and the logarithm of the measured gamma-ray attenuations respectively.

30. A system according to claim 29, where the processor is further operable to add a positive number to the measured attenuations prior to forming the logarithm to ensure that the logarithm is finite.

31. A system according to claim 30, where the processor is further operable to truncate the elements of each of the neutron mass attenuation and gamma-ray mass attenuation matrices to a predetermined range to remove elements having negative values.

32. A system according to claim 31, where the processor is further operable to scale the neutron and gamma-ray mass attenuation matrices to a range 0 to 1.

33. A system according to claim 32, where the processor is operable to calculate two copies of both the neutron and gamma-ray mass attenuation matrices, one having a spatial resolution substantially equal to that of the neutron image and one with a spatial resolution substantially equal to that of the gamma-ray image, where these two resolutions are different.

34. A system according to claim 33, where the processor is operable to calculate the elements of the composition matrix R according to the formula $R_{ij}=(a_1 n_{ij}+a_2 g_{ij})/(a_3 n_{ij}+a_4 g_{ij}+e)$ where $a_1, a_2, a_3, a_4$ are weighting parameters and e is a positive number chosen to prevent the denominator tending to zero.

35. A system according to claim 34, where the elements of the composition matrix R are calculated from the neutron and gamma-ray mass attenuation matrices with the lowest spatial resolution.

36. A system according to claim 35, where the processor is further operable to apply a spatial filter for smoothing to the calculated composition matrix R.

37. A system according to claim 36, where the spatial filler for smoothing replaces each element with a normalised, weighted average of neighbouring elements, where the weights are computed as a product of a geometric distance function and a radiometric distance function such that an element with closer geometric and radiometric distances from a central element has a stronger influence on the smoothing result, where geometric distances are calculated using true distances between the central element and its neighbouring elements which are independent of image resolutions and the radiometric distances are calculated by absolute or fractional differences of the attenuations values between the central element and its neighbouring elements.

38. A system according to any one of claim 34, where the processor is further operable to apply a spatial filter for smoothing to the neutron and gamma-ray mass attenuation matrices before calculating the composition matrix R.

39. A system according to claim 27, where the processor is further operable to calculate the elements of the density matrix X according to the formula $X_{ij}=g_{ij}*f(g_{ij})+b*n_{ij}*(1-f(g_{ij}))$, where $f(g_{ij})$ is a function which is substantially equal to unity over most of its range but tends to zero as its argument tends to 1 and b is a weighting parameter that accounts for the different attenuations of gamma-rays and neutrons.

40. A system according to claim 39, where b is a fixed parameter.

41. A system according to claim 40, where the function f(x) has the form $(1-x)$ where the exponent p lies in the range 0-1.

42. A system according to claim 41, where the elements of the density matrix X are calculated from the neutron and gamma-ray mass attenuation matrices with the highest spatial resolution.

43. A system according to claim 42, where the processor is further operable to apply a spatial filter for smoothing to the neutron and gamma-ray mass attenuation matrices before calculating the density matrix X.

44. A system according to claim 43, where the processor is further operable to apply a spatial filter for sharpening to the calculated density matrix X.

45. A system according to claim 44, where the spatial filter for sharpening replaces each element with a normalised weighted average of neighbouring elements, where the weights are computed as a product of a geometric distance function and a radiometric distance function such that an element with a closer geometric distance and a greater radiometric distance from a central element has stronger influence on sharpening result, where the geometric distances are calculated using the true distances between the central element and its neighbouring elements which are independent of image resolutions and the radiometric distances are calculated by absolute or fractional differences of the attenuation values between the central element and its neighbouring elements.

46. A system according to claim 27, where the processor is further operable to calculate the elements of the quality matrix Q according to the formula $Q_{ij}=q(n_{ij},g_{ij})$, where the function $q(n_{ij},g_{ij})$ is substantially equal to unity except for where either of its arguments tends to either 0 or 1, in which case the value of $q(n_{ij},g_{ij})$ tends to zero.

47. A system according to claim 46, where $g(n_{ij},g_{ij})$ has the function form $Q_{ij}=[n_{ij}/2+g_{ij})*(1-n_{ij})/2+(1-g_{ij})]^\alpha$, or $Q_{ij}=(n_{ij}*g_{ij})^\alpha*[\max(1-n_{ij},1-g_{ij})]^\beta$, where β and β are positive real numbers.

48. A system according to claim 47, where the processor is further operable to calculate the elements of the quality matrix Q from the neutron and gamma-ray mass attenuation matrices with the lowest spatial resolution.

49. A system according to claim 27, where the processor is further operable to interpolate the composition matrix R and quality matrix Q to increase the resolution so as to match the resolution of the density matrix X.

* * * * *